(12) United States Patent
Criere et al.

(10) Patent No.: US 8,563,042 B2
(45) Date of Patent: *Oct. 22, 2013

(54) PHARMACEUTICAL COMPOSITION CONTAINING FENOFIBRATE AND METHOD FOR THE PREPARATION THEREOF

(75) Inventors: Bruno Criere, Gravigny (FR); Pascal Suplie, Montaure (FR); Philippe Chenevier, Montreal (CA)

(73) Assignee: Ethypharm, Sanit-Cloud (FR)

( * ) Notice: Subject to any disclaimer, the term of this patent is extended or adjusted under 35 U.S.C. 154(b) by 24 days.

This patent is subject to a terminal disclaimer.

(21) Appl. No.: 12/823,900

(22) Filed: Jun. 25, 2010

(65) Prior Publication Data

US 2011/0159082 A1    Jun. 30, 2011

Related U.S. Application Data

(63) Continuation of application No. 11/509,806, filed on Aug. 25, 2006, which is a continuation of application No. 10/030,262, filed as application No. PCT/FR00/01971 on Jul. 7, 2000, now Pat. No. 7,101,574.

(51) Int. Cl.
*A61K 9/14* (2006.01)
*A61K 9/64* (2006.01)
*A61K 9/56* (2006.01)

(52) U.S. Cl.
USPC ........... 424/489; 424/456; 424/459; 424/462; 514/49

(58) Field of Classification Search
None
See application file for complete search history.

(56) References Cited

U.S. PATENT DOCUMENTS

| | | |
|---|---|---|
| 3,914,286 A | 10/1975 | Mieville |
| 4,058,552 A | 11/1977 | Mieville |
| 4,344,934 A | 8/1982 | Martin et al. |
| 4,412,986 A | 11/1983 | Kawata et al. |
| 4,717,569 A | 1/1988 | Harrison et al. |
| 4,752,470 A | 6/1988 | Mehta |
| 4,800,079 A | 1/1989 | Boyer |
| 4,895,726 A | 1/1990 | Curtet |
| 5,145,684 A | 9/1992 | Liversidge et al. |
| 5,545,628 A | 8/1996 | Deboeck et al. |

(Continued)

FOREIGN PATENT DOCUMENTS

| | | |
|---|---|---|
| EP | 012523 | 6/1980 |
| EP | 0164 959 | 12/1985 |

(Continued)

OTHER PUBLICATIONS

El-Arini et al. "Dissolution Properties of Praziquantel-PVP systems," *Pharmaceutical Acta Helvetiae* v. 72, pp. 89-94 (1998).

U.S. Department of Health and human Services Food and Drug Administration Center for Drug Evaluation and Research 9CDER) Oct. 1997 pp. 1-8.

(Continued)

*Primary Examiner* — Lakshmi Channavajjala
(74) *Attorney, Agent, or Firm* — RatnerPrestia

(57) ABSTRACT

The invention concerns a pharmaceutical composition containing micronized fenofibrate, a surfactant and a binding cellulose derivative, as solubilizing adjuvant, preferably hydroxypropylmethylcellulose. The cellulose derivative represents less than 20 wt. % of the composition. The association of micronized fenofibrate with a binding cellulose derivative, as solubilizing adjuvant and a surfactant enables enhanced bioavailability of the active principle. The invention also concerns a method for preparing said composition without using any organic solvent.

12 Claims, 4 Drawing Sheets

(56) References Cited

U.S. PATENT DOCUMENTS

| | | | |
|---|---|---|---|
| 5,558,879 | A | 9/1996 | Chen et al. |
| 5,776,495 | A | 7/1998 | Duclos et al. |
| 5,840,330 | A | 11/1998 | Stemmle et al. |
| 6,074,670 | A | 6/2000 | Stamm et al. |
| 6,277,405 | B1 | 8/2001 | Stamm et al. |
| 6,368,620 | B2 | 4/2002 | Liu et al. |
| 6,423,517 | B2 | 7/2002 | Becker et al. |
| 6,667,064 | B2 | 12/2003 | Surette |
| 6,696,084 | B2 | 2/2004 | Pace et al. |
| 7,101,574 | B1 | 9/2006 | Criere et al. |
| 7,863,331 | B2 * | 1/2011 | Criere et al. ............... 514/571 |
| 2004/0137055 | A1 | 7/2004 | Criere et al. |
| 2006/0083783 | A1 | 4/2006 | Doyle, Jr. et al. |
| 2008/0248101 | A1 | 10/2008 | Criere et al. |

FOREIGN PATENT DOCUMENTS

| | | |
|---|---|---|
| EP | 0 330 532 | 8/1989 |
| EP | 0 514 967 A | 11/1992 |
| EP | 0 519 144 A | 12/1992 |
| EP | 793 958 A2 | 9/1997 |
| HU | 219 341 B | 3/1997 |
| WO | WO 82/01649 | 5/1982 |
| WO | WO 98/31360 | 7/1988 |
| WO | WO 96/01621 | 1/1996 |
| WO | WO 98/00116 A | 1/1998 |
| WO | WO 98/31361 A | 7/1998 |
| WO | WO 01/03693 A1 | 1/2001 |

OTHER PUBLICATIONS cancerweb.ncl.ac.uk/cgi-bin/omd?inert 1997, 1 page.
"TriCor, Micronized Fenofibrate, Now Available in U.S. For High Triglycerides" 2 pages, Jun. 2, 1998 http://www.pslgroup.com/dg/81D66.htm.
International Search Report issued Oct. 26, 2000 in corresponding PCT/FR 00/01971.
The Merck Index—An Encyclopedia of Chemicals, Drugs and Biologicals. Twelfth edition. (1996) p. 3260.
The Merck Index—An Encyclopedia of Chemicals, Drugs and Biologicals. Thirteenth edition. (2001) p. 3238.
A. Munoz et al., "Micronised Fenofibrate", *Atherosclerosis* 110 (Suppl.) (1994) S45-S48, Elsevier Science, Ireland.
D.F. Temeljotov et al., "Solubilization and Dissolution Enhancement for Sparingly Soluble Fenofibrate", *Acta. Pharm.* 46 (1996) 131-136.
I. Ghebre-Sellassie "Pellets: A General Overview", *Pharmaceutical Pelletization Technology, Drugs and the Pharmaceutical Sciences*, 37, pp. 2, 3, 234 (1989), edited by Isaac Ghebre-Sellassie, Marcel Dekker, Inc. NY NY.
R. Bianchini et al., "Influence of Drug Loading on Coated Beads Release Using Air Suspension Technique", *Boll. Chim. Farmaceutico*, 128 (Dec. 12, 1989) pp. 373-379.
Dr. Bernhard Luy, "Methods of Pellet Production", Presented at Glatt Symposium, Strasbourg (Oct. 1992) pp. 1-12, with curriculum vitae.
A. Kuchiki et al., "Stable Solid Dispersion System Against Humidity", *Yakuzaigaku* 44(1) 31-37 (1984) pp. 1-13.
JP Guichard et al., "A New Formulation of Fenofibrate: Suprabioavailable Tablets", Current Medical Research and Opinion 16(2) (2000) pp. 134-138, Laboratoires Fournier, France.

* cited by examiner

PHARMACEUTICAL COMPOSITION CONTAINING FENOFIBRATE AND METHOD FOR THE PREPARATION THEREOF

CROSS-REFERENCE TO RELATED APPLICATIONS

This application is a continuation of application Ser. No. 11/509,806, filed Aug. 25, 2006, which is a continuation of application Ser. No. 10/030,262, filed Apr. 17, 2002, now U.S. Pat. No. 7,101,574 which is a National Stage of Application No. PCT/FR00/01971, filed Jul. 7, 2000, which claims the benefit of French Application No. 99/08,923, filed on Jul. 9, 1999.

The present invention relates to a novel pharmaceutical composition containing fenofibrate.

Fenofibrate is recommended in the treatment of adult endogenous hyperlipidemias, of hypercholesterolemias and of hypertriglyceridemias. A treatment of 300 to 400 mg of fenofibrate per day enables a 20 to 25% reduction of cholesterolemia and a 40 to 50% reduction of triglyceridemia to be obtained.

The major fenofibrate metabolite in the plasma is fenofibric acid. The half-life for elimination of fenofibric acid from the plasma is of the order of 20 hours. Its maximum concentration in the plasma is attained, on average, five hours after ingestion of the medicinal product. The mean concentration in the plasma is of the order of 15 micrograms/ml for a dose of 300 mg of fenofibrate per day. This level is stable throughout treatment.

Fenofibrate is an active principle which is very poorly soluble in water, and the absorption of which in the digestive tract is limited. An increase in its solubility or in its rate of solubilization leads to better digestive absorption.

Various approaches have been explored in order to increase the rate of solubilization of fenofibrate: micronization of the active principle, addition of a surfactant, and comicronization of fenofibrate with a surfactant.

Patent EP 256 933 describes fenofibrate granules in which the fenofibrate is micronized in order to increase its bioavailability. The crystalline fenofibrate microparticles are less than 50 μm in size. the binder used is polyvinylpyrrolidone. The document suggests other types of binder, such as methacrylic polymers, cellulose derivatives and polyethylene glycols. The granules described in the examples of EP 256 933 are obtained by a method using organic solvents.

Patent EP 330 532 proposes improving the bioavailability of fenofibrate by comicronizing it with a surfactant, such as sodium lauryl sulfate. The comicronizate is then granulated by wet granulation in order to improve the flow capacities of the powder and to facilitate the transformation into gelatin capsules. This comicronization allows a significant increase in the bioavailability compared to the use of fenofibrate described in EP 256 933. The granules described in EP 330 532 contain polyvinylpyrrolidone as a binder.

This patent teaches that the comicronization of fenofibrate with a solid surfactant significantly improves the bioavailability of the fenofibrate compared to the use of a surfactant, of micronization or of the combination of a surfactant and of micronized fenofibrate.

Patent WO 98/31361 proposes improving the bioavailability of the fenofibrate by attaching to a hydrodispersible inert support micronized fenofibrate, a hydrophilic polymer and, optionally, a surfactant. The hydrophilic polymer, identified as polyvinyl-pyrrolidone, represents at least 20% by weight of the composition described above.

This method makes it possible to increase the rate of dissolution of the fenofibrate, and also its bioavailability. However, the preparation method according to that patent is not entirely satisfactory since it requires the use of a considerable amount of PVP and of the other excipients. The example presented in that patent application refers to a composition containing only 17.7% of fenofibrate expressed as a mass ratio. This low mass ratio for fenofibrate leads to a final form which is very large in size, hence a difficulty in administering the desired dose of fenofibrate, or the administration of two tablets.

In the context of the present invention, it has been discovered that the incorporation of a cellulose derivative, used as a binder and solubilization adjuvant, into a composition containing micronized fenofibrate and a surfactant makes it possible to obtain a bioavailability which is greater than for a composition containing a comicronizate of fenofibrate and of a surfactant.

A subject of the present invention is therefore a pharmaceutical composition containing micronized fenofibrate, a surfactant and a binding cellulose derivative, which is a solubilization adjuvant, preferably hydroxypropylmethylcellulose (HPMC).

The composition of the invention is advantageously provided as gelatin capsules containing powder or granules, preferably in the form of granules. These granules may in particular be prepared by assembly on neutral microgranules, by spraying an aqueous solution containing the surfactant, the solubilized binding cellulose derivative and the micronized fenofibrate in suspension, or by wet granulation of powder, according to which the constituents, including in particular the micronized fenofibrate, the surfactant and the cellulose derivative, are granulated by wet granulation using an aqueous wetting solution, dried and calibrated.

The pharmaceutical composition according to the present invention has a high proportion of fenofibrate; it may therefore be provided in a formulation which is smaller in size than the formulations of the prior art, which makes this composition according to the invention easy to administer.

The amount of fenofibrate is greater than or equal to 60% by weight, preferably greater than or equal to 70% by weight, even more preferably greater than or equal to 75% by weight, relative to the weight of the composition.

In the context of the present invention, the fenofibrate is not comicronized with a surfactant. On the contrary, it is micronized alone and then combined with a surfactant and with the binding cellulose derivative, which is a solubilization adjuvant.

The surfactant is chosen from surfactants which are solid or liquid at room temperature, for example sodium lauryl sulfate, POLYSORBATE® 80 or MONTANE® 20, preferably sodium lauryl sulfate.

The fenofibrate/HPMC ratio is preferably between 5/1 and 15/1.

The surfactant represents between 1 and 10%, preferably between 3 and 5%, by weight relative to the weight of fenofibrate.

The binding cellulose derivative represents between 2 and 15%, preferably between 5 and 12%, by weight of the composition.

Hydroxypropylmethylcellulose is preferably chosen, the apparent viscosity of which is between 2.4 and 18 cP, and even more preferably between 2.4 and 3.6 cP, such as for example PHARMACOAT 603®.

The mean size of the fenofibrate particles is less than 15 μm, preferably 10 μm, even more preferably less than 8 μm.

The composition of the invention may also contain at least one excipient such as diluents, for instance lactose, antifoaming agents, for instance DIMETHICONE® and SIMETHICONE®, or lubricants, for instance talc.

The pharmaceutical composition of the invention advantageously consists of granules in an amount equivalent to a dose of fenofibrate of between 50 and 300 mg, preferably equal to 200 mg.

The present invention also relates to a method for preparing the powder or the granules, the composition of which is described above. This method uses no organic solvent.

According to a first variant, the granules are prepared by assembly on neutral microgranules.

The neutral microgranules have a particle size of between 200 and 1 000 microns, preferably between 400 and 600 microns.

The assembly is carried out in a sugar-coating pan, in a perforated coating pan or in a fluidized airbed, preferably in a fluidized airbed.

The assembly on neutral microgranules is carried out by spraying an aqueous solution containing the surfactant, the solubilized binding cellulose derivative, and the micronized fenofibrate in suspension.

According to a second variant, the granules are obtained by wet granulation of powder. The granulation enables the powders to be made dense and makes it possible to improve their flow properties. It also allows better preservation of the homogeneity, by avoiding the various constituents becoming unmixed.

The micronized fenofibrate, the surfactant, the cellulose derivative and, optionally, the other excipients are mixed, granulated, dried and then calibrated. The wetting solution may be water or an aqueous solution containing the binding cellulose derivative and/or the surfactant.

According to a particular embodiment, the fenofibrate and the other excipients are mixed in a planetary mixer. The wetting solution is added directly to the mixture. The wet mass obtained is granulated with an oscillating granulator, and then dried in an oven. The granules are obtained after passage over an oscillating calibrator.

Figure 1:
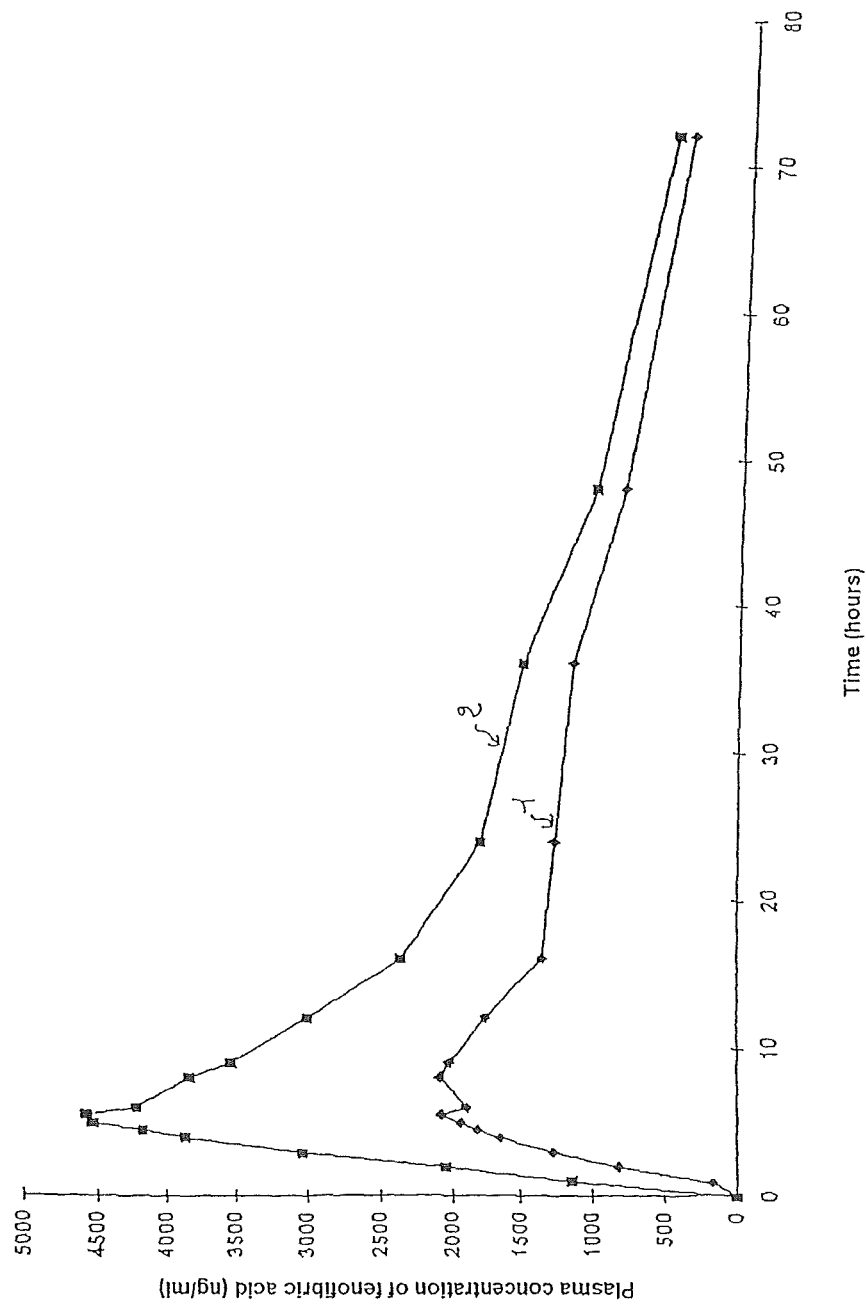
FIG. 1 represents the in vivo release profile of the formulation of example 1C and of a formulation of the prior art in fasting individuals.

The invention is illustrated in a nonlimiting way by the following examples.

EXAMPLE 1

Granules

1A) Microgranules (XFEN 1735)

The microgranules are obtained by spraying an aqueous suspension onto neutral cores. The composition is given in the following table:

| Formula | Amount (percentage by mass) |
| --- | --- |
| Micronized fenofibrate | 64.5 |
| Neutral microgranules | 21 |
| HPMC (Pharmacoat 603 ®) | 11.2 |
| Polysorbate ® 80 | 3.3 |
| Fenofibrate content | 645 mg/g |

The in vitro dissolution was determined according to a continuous flow cell method with a flow rate of 8 ml/min of sodium lauryl sulfate at 0.1 N. The percentages of dissolved product as a function of time, in comparison with a formulation of the prior art, LIPANTHYL 200 M, are given in the following table.

| | Time (min) | |
| --- | --- | --- |
| | 15 | 30 |
| Example 1A (% dissolved) | 73 | 95 |
| Lipanthyl 200 M (% dissolved) | 47.3 | 64.7 |

Formulation 1A dissolves more rapidly than LIPANTHYL 200 M.

1B) Microgranules (X FEN 1935)

The mean size of the fenofibrate particles is equal to 6.9±0.7 microns.

The microgranules are obtained by spraying an aqueous suspension onto neutral cores. The suspension contains micronized fenofibrate, sodium lauryl sulfate and HPMC.

The assembly is carried out in a Huttlin fluidized airbed (rotoprocess).

The formula obtained is given below.

| FORMULA | AMOUNT (percentage by mass) |
| --- | --- |
| Micronized fenofibrate | 65.2 |
| Neutral microgranules | 20.1 |
| HPMC (Pharmacoat 603 ®) | 11.4 |
| Sodium lauryl sulfate | 3.3 |
| Fenofibrate content | 652 mg/g |

The size of the neutral microgranules is between 400 and 600 μm.

1C) Gelatin Capsules of Microgranules (Y FEN 001)

Microgranules having the following composition are prepared:

| RAW MATERIALS | AMOUNT (percentage by mass) |
| --- | --- |
| Micronized fenofibrate | 67.1 |
| Neutral microgranules | 17.2 |
| Pharmacoat 603 ® (HPMC) | 11.7 |
| Sodium lauryl sulfate | 3.3 |
| 35% dimethicone emulsion | 0.2 |
| Talc | 0.5 |
| Fenofibrate content | 671 mg/g | according to the method described in paragraph 1A).

The microgranules obtained are distributed into size 1 gelatin capsules, each containing 200 mg of fenofibrate.

The in vitro dissolution is determined according to a continuous flow cell method with a flow rate of 8 ml/min of sodium lauryl sulfate at 0.1 N. The comparative results with a formulation of the prior art, LIPANTHYL 200 M, are given in the following table.

|  | Time (min) | |
| --- | --- | --- |
|  | 15 | 30 |
| Example 1C (% dissolved) | 76 | 100 |
| Lipanthyl 200 M (% dissolved) | 47.3 | 64.7 |

Formula 1C dissolves more rapidly than LIPANTHYL 200 M.

The gelatin capsules are conserved for 6 months at 40° C./75% relative humidity. The granules are stable under these accelerated storage conditions. In vitro dissolution tests (in continuous flow cells with a flow rate of 8 ml/min of sodium lauryl sulfate at 0.1 N) were carried out. The percentages of dissolved product as a function of time for gelatin capsules conserved for 1, 3 and 6 months are given in the following table.

|  | Conservation time | | |
| --- | --- | --- | --- |
| Dissolution time (min) | 1 month (% dissolved product) | 3 months (% dissolved product) | 6 months (% dissolved product) |
| 5 | 25.1 | 23.0 | 20.1 |
| 15 | 71.8 | 65.6 | 66.5 |
| 25 | 95.7 | 88.7 | 91.0 |
| 35 | 104.7 | 98.7 | 98.2 |
| 45 | 106.4 | 100.2 | 99.1 |
| 55 | 106.7 | 100.5 | 99.5 |
| 65 | 106.8 | 100.6 | 99.7 |

The evolution of the content of active principle during storage is given in the following table.

|  | Conservation time | | | |
| --- | --- | --- | --- | --- |
|  | 0 | 1 month | 3 months | 6 months |
| Content (mg/gelatin Capsule) | 208.6 | 192.6 | 190.8 | 211.7 |

Pharmacokinetic Study Carried Out in Fasting Individuals

The in vivo release profile of the gelatin capsules containing the YFEN 01 granules at a dose of 200 mg of fenofibrate is compared with that of the gelatin capsules marketed under the trademark LIPANTHYL 200 M.

This study is carried out in 9 individuals. Blood samples are taken at regular time intervals and fenofibric acid is assayed.

The results are given in the following table and FIG. 1.

| Pharmacokinetic parameters | Lipanthyl 200M | Example 1C |
| --- | --- | --- |
| $AUC_{0-t}$ (µg · h/ml) | 76 | 119 |
| $AUC_{inf}$ (µg · h/ml) | 96 | 137 |
| $C_{max}$ (µg/ml) | 2.35 | 4.71 |
| $T_{max}$ (hours) | 8.0 | 5.5 |
| Ke (1/hour) | 0.032 | 0.028 |
| Elim ½ (hours) | 26.7 | 24.9 |

The following abbreviations are used in the present application:

$C_{max}$: maximum concentration in the plasma, $T_{max}$: time required to attain the Cmax, $Elim_{1/2}$: plasmatic half-life, $AUC_{0-t}$: area under the curve from 0 to t, $AUC_{0-\infty}$: area under the curve from 0 to ∞, Ke: elimination constant.

The results obtained for LIPANTHYL 200 M and for the product of example 1C are represented on FIG. 1 by curves 1 and 2, respectively.

These results show that the composition according to the present invention has a bioavailability which is greater than that of LIPANTHYL 200 M in fasting individuals.

Pharmacokinetic Study Carried Out in Individuals Who have Just Eaten

The in vivo release profile of the gelatin capsules containing the YFEN 01 granules at a dose of 200 mg of fenofibrate is compared with that of the gelatin capsules marketed under the trademark LIPANTHYL 200 M.

This study is carried out in 18 individuals. Blood samples are taken at regular time intervals and fenofibric acid is assayed.

The results are given in the following table and FIG. 2.

| Pharmacokinetic parameters | Lipanthyl 200M | Example 1C |
| --- | --- | --- |
| $AUC_{0-t}$ (µg · h/ml) | 244 | 257 |
| $AUC_{inf}$ (µg · h/ml) | 255 | 270 |
| $C_{max}$ (µg/ml) | 12 | 13 |
| $T_{max}$ (hours) | 5.5 | 5.5 |
| Ke (1/hour) | 0.04 | 0.04 |
| Elim ½ (hours) | 19.6 | 19.3 |

Figure 2:
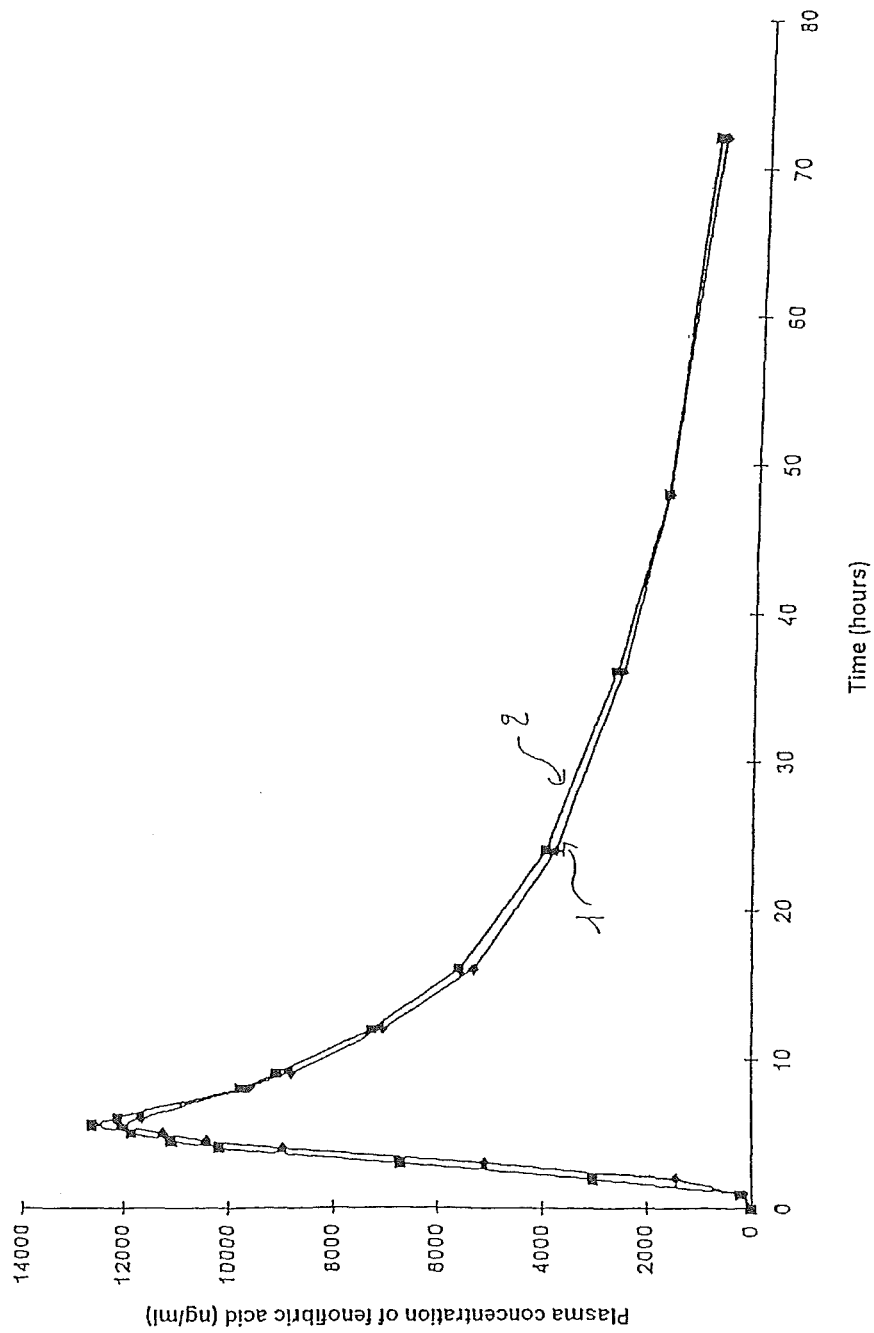
FIG. 2 represents the in vivo release profile of the formulation of example 1C and of a formulation of the prior art in individuals who have just eaten.

The results obtained for LIPANTHYL 200 M and for the product of example 1C are represented on FIG. 2 by curves 1 and 2, respectively.

These results show that the composition according to the present invention is bioequivalent to that of LIPANTHYL 200 M in individuals who have just eaten.

EXAMPLE 2

Powder

2A) Granules (X FEN 1992)

Granules having the following composition are prepared

| FORMULA | PERCENTAGE BY MASS |
|---|---|
| Micronized fenofibrate | 71 |
| Lactose | 21.5 |
| HPMC (Pharmacoat 603 ®) | 5 |
| Sodium lauryl sulfate | 2.5 |

The micronized fenofibrate, the HPMC and the lactose are mixed using a planetary mixer. This mixture is granulated in the presence of a solution of sodium lauryl sulfate.

The flow time of the granules is 7 s. The compacting capacity and the particle size distribution are given in the following tables. These measurements were carried out in accordance with the standards of the European Pharmacopoeia.

| Compacting capacity (X FEN 1992) | |
|---|---|
| V0 | 204 ml |
| V10 | 186 ml |
| V500 | 168 ml |
| V1250 | 164 ml |
| V10-V500 | 22 ml |

| Particle size distribution (X FEN 1992) | |
|---|---|
| Sieve mesh size (mm) | % of oversize mass |
| 0.6 | 8 |
| 0.5 | 9 |
| 0.355 | 12 |
| 0.2 | 30 |
| 0.1 | 23 |
| 0 | 18 |

2B) Gelatin Capsules of Granules (Y FEN 002)

Preparation

The micronized fenofibrate is mixed in a PMA mixer (Niro Fielder) with lactose and HPMC, and then wetted with an aqueous solution of sodium lauryl sulfate. The mass obtained is granulated by passage over an oscillating granulator, dried and then calibrated on a sieve with a mesh size of 1.25 mm.

The granules are then packaged in size 1 gelatin capsules at doses of 200 mg of fenofibrate.

Granules of the following composition are obtained.

| FORMULA | PERCENTAGE BY MASS |
|---|---|
| Micronized fenofibrate | 70 |
| Lactose | 21.5 |
| Pharmacoat 603 ® (HPMC) | 5 |
| Sodium lauryl sulfate | 3.5 |
| Content | 700 mg/g |

Properties of the Granules

The flow time of the granules is 6 s. The compacting capacity and the particle size distribution are given in the following tables. These measurements were carried out in accordance with the standards of the European Pharmacopoeia.

| Compacting capacity (Y FEN 002) | |
|---|---|
| V0 | 216 ml |
| V10 | 200 ml |
| V500 | 172 ml |
| V1250 | 170 ml |
| V10-V500 | 28 ml |

| Particle size distribution (Y FEN 002) | |
|---|---|
| Sieve mesh size (mm) | % of oversize mass |
| 0.6 | 5 |
| 0.5 | 7 |
| 0.355 | 11 |
| 0.2 | 30 |
| 0.1 | 25 |
| 0 | 22 |

The in vitro dissolution is determined according to a continuous flow cell method with a flow rate of 8 ml/min of sodium lauryl sulfate at 0.1 N. The comparative results for a formulation of the prior art, LIPANTHYL 200 M, are given in the following table.

| | Time (min) | |
|---|---|---|
| | 15 | 30 |
| Example 2B (% dissolved) | 82.2 | 88.5 |
| Lipanthyl 200M (% dissolved) | 47.3 | 64.7 |

Formulation 2B dissolves more rapidly than Lipanthyl 200 M.

Stability Tests

The gelatin capsules conserved at 40° C./75% relative humidity are stable for 6 months.

In vitro dissolution tests (in continuous flow cells with a flow rate of 8 ml/min of sodium lauryl sulfate at 0.1 N) were carried out. The percentages of dissolved product as a function of time for gelatin capsules conserved for 1, 3 and 6 months are given in the following table.

| | Conservation time | | |
|---|---|---|---|
| Dissolution time (min) | 1 month (% dissolved product) | 3 months (% dissolved product) | 6 months (% dissolved product) |
| 5 | 54.2 | 52.9 | 49.0 |
| 15 | 81.1 | 75.8 | 82.2 |
| 25 | 86.4 | 79.6 | 87.2 |
| 35 | 88.8 | 81.6 | 89.8 |
| 45 | 90.7 | 82.9 | 91.5 |
| 55 | 92.1 | 83.9 | 92.7 |
| 65 | 93.2 | 84.7 | 93.6 |

The evolution of the content of active principle during storage is given in the following table.

|  | Conservation time | | | |
| --- | --- | --- | --- | --- |
|  | 0 | 1 month | 3 months | 6 months |
| Content (mg/gelatin capsule) | 196.6 | 190.0 | 199.8 | 203.3 |

Pharmacokinetic Study Carried Out in Fasting Individuals

The in vivo release profile of the gelatin capsules containing the YFEN 002 granules at doses of 200 mg of fenofibrate is compared with that of the gelatin capsules marketed under the trademark LIPANTHYL 200 M.

This study is carried out in 9 individuals. Blood samples are taken at regular time intervals and fenofibric acid is assayed.

The results are given in the following table and FIG. 3.

| Pharmacokinetic parameters | Lipanthyl 200M | Example 2B |
| --- | --- | --- |
| $AUC_{0-t}$ (µg · h/ml) | 76 | 70 |
| $AUC_{inf}$ (µg · h/ml) | 96 | 82 |
| $C_{max}$ (µg/ml) | 2.35 | 2.8 |
| $T_{max}$ (hours) | 8.0 | 5.5 |
| Ke (1/hour) | 0.032 | 0.033 |
| Elim ½ (hours) | 26.7 | 23.1 |

Figure 3:
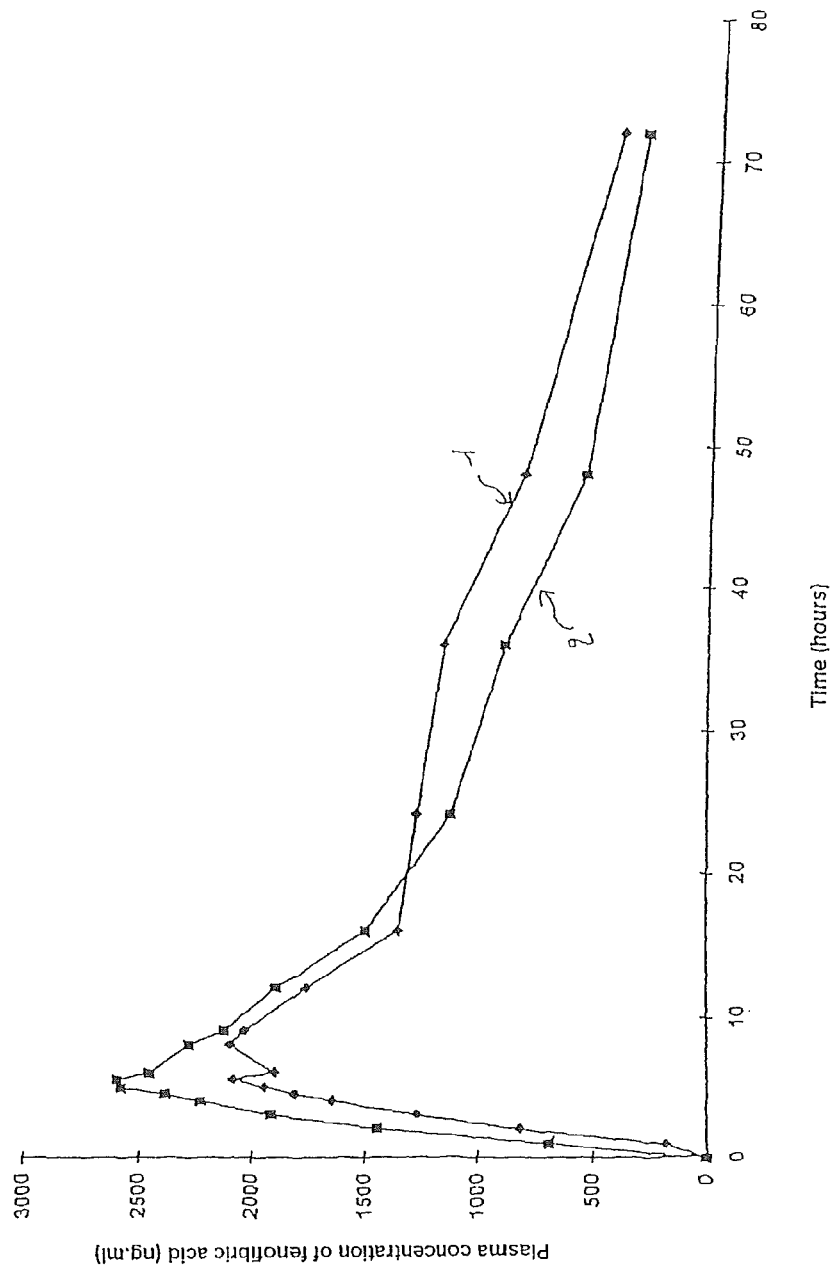
FIG. 3 represents the in vivo release profile of the formulation of example 2B and of a formulation of the prior art in fasting individuals.

The results obtained for LIPANTHYL 200 M and for the product of example 2B are represented on FIG. 3 by curves 1 and 2, respectively.

These results show that the composition of example 2B is bioequivalent to that of LIPANTHYL 200 M in fasting individuals.

COMPARATIVE EXAMPLE 3

Batch ZEF 001

This example illustrates the prior art.

It combines micronization of fenofibrate and the use of a surfactant. It differs from the present invention by the use of the mixture of binding excipients consisting of a cellulose derivative other than HPMC: Avicel PH 101 and polyvinylpyrrolidone (PVP K30).

It is prepared by extrusion-spheronization.

Theoretical Formula

| Products | Theoretical amount (%) |
| --- | --- |
| Micronized fenofibrate | 75.08 |
| Montanox 80 ® | 4.72 |
| Avicel PH 101 ® | 5.02 |
| PVP K 30 ® | 4.12 |
| Explotab ® | 11.06 |

In Vitro Dissolution Profile

The in vitro dissolution is determined according to a continuous flow cell method with a flow rate of 8 ml/min of sodium lauryl sulfate at 0.1 N. The comparative results with LIPANTHYL 200 M are given in the following table.

|  | Time (min) | |
| --- | --- | --- |
|  | 15 | 30 |
| Example 3 (% dissolved) | 24 | 40 |
| Lipanthyl 200M (% dissolved) | 47.3 | 64.7 |

The dissolution is slower than that observed for LIPANTHYL 200 M.

Pharmacokinetic Study Carried Out in Fasting Individuals

The in vivo release profile of the gelatin capsules containing the ZEF 001 granules at doses of 200 mg of fenofibrate is compared with that of the gelatin capsules marketed under the trademark LIPANTHYL 200 M.

This study is carried out in 5 fasting individuals receiving a single dose. Blood samples are taken at regular time intervals and fenofibric acid is assayed.

The results are given in the following table and FIG. 4.

| Pharmacokinetic parameters | Lipanthyl 200M | Example 3 |
| --- | --- | --- |
| $AUC_{0-t}$ (µg · h/ml) | 92 | 47 |
| $AUC_{inf}$ (µg · h/ml) | 104 | 53 |
| $C_{max}$ (µg/ml) | 3.5 | 1.7 |
| $T_{max}$ (hours) | 5.6 | 4.6 |
| Ke (1/hour) | 0.04 | 0.038 |
| Elim ½ (hours) | 18.9 | 20.3 |

Figure 4:
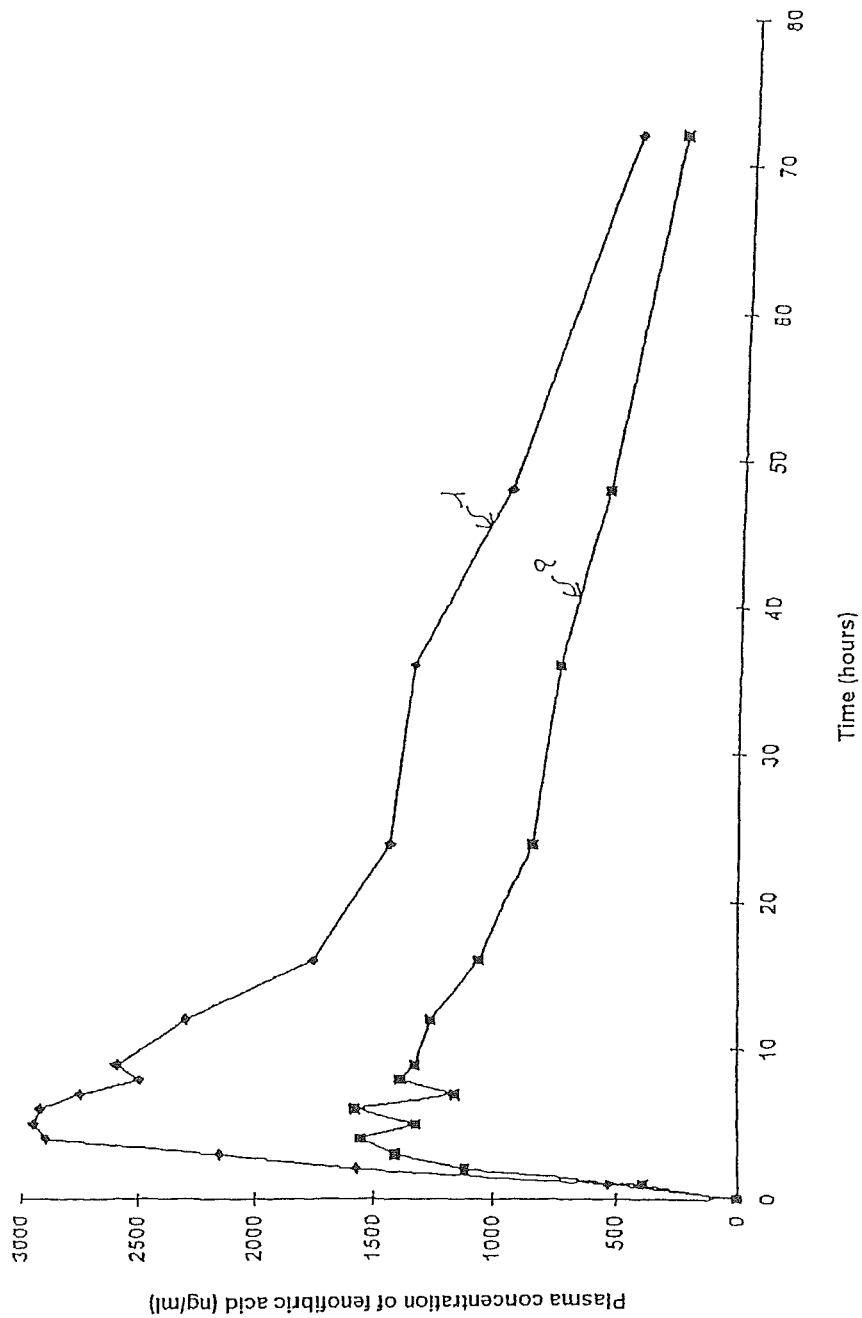
FIG. 4 represents the in vivo release profile of the formulation of comparative example 3 and of a formulation of the prior art in individuals who have just eaten.

The results obtained for LIPANTHYL 200 M and for the product of example 3 are represented on FIG. 4 by curves 1 and 2, respectively.

These results show the greater bioavailability of LIPANTHYL 200 M compared with this formulation based on the prior art.

Example 3 shows that combining the knowledge of the prior art (namely micronization or use of surfactants) does not make it possible to obtain rapid dissolution of fenofibrate. This results in low bioavailability compared with LIPANTHYL 200 M.

The compositions prepared according to the present invention show more rapid dissolution than the formula of the prior art and improved bioavailability.

The invention claimed is:

1. A pharmaceutical composition comprising between 50 and 300 mg of micronized fenofibrate coated on neutral microgranules in a single active layer comprising said micronized fenofibrate, as surfactant and hydroxypropyl methyl cellulose (HPMC), wherein the fenofibrate/HPMC ratio is between 5/1 and 15/1 and the surfactant represents between 1 and 10% by weight relative to the weight of fenofibrate.

2. The composition of claim 1 in a capsule.

3. The composition of claim 1, wherein the dose of fenofibrate is 50 mg to 200 mg.

4. The composition of claim 1, wherein the neutral microgranules have a particle size between 200 and 1000 microns.

5. The composition of claim 4, wherein the neutral microgranules have a particle size between 400 and 600 microns.

6. The composition of claim 1, wherein the mean size of the fenofibrate micronized particles is less than 8 μm.

7. The composition of claim 1, wherein the surfactant is sodium lauryl sulphate.

8. The composition of claim 1, wherein HPMC represents between 3 and 5% by weight relative to the weight of fenofibrate.

9. The pharmaceutical composition of claim 1, which, when administered to a patient in a fasting state at a dose of 200 mg fenofibrate, achieves a Cmax of at least 4 micrograms/ml.

10. The pharmaceutical composition of claim 1, which, when administered to a patient in a fasting state at to dose of 200 mg fenofibrate, achieves AUC of at least 119.

11. The pharmaceutical composition of claim 1, wherein at least 20% of said fenofibrate is dissolved at 5 minutes, as measured using a continuous flow cell method with a flow rate of 8 ml/min of sodium lauryl sulfate at 0.1 N.

12. The pharmaceutical composition of claim 1, wherein at least 65% of said fenofibrate is dissolved at 15 minutes, as measured using a continuous flow cell method with a flow rate of 8 ml/min of sodium lauryl sulfate at 0.1 N.

* * * * *